United States Patent
Chern et al.

(10) Patent No.: US 7,259,174 B2
(45) Date of Patent: Aug. 21, 2007

(54) IMIDAZOLIDINONE COMPOUNDS

(75) Inventors: Jyh-Haur Chern, Taipei (TW);
Shin-Ru Shih, Tao-Yuan (TW);
Chih-Shiang Chang, Taipei (TW);
Chung-Chi Lee, Taipei (TW);
Yen-Chun Lee, Taitung (TW)

(73) Assignee: National Health Research Institutes (TW)

( * ) Notice: Subject to any disclaimer, the term of this patent is extended or adjusted under 35 U.S.C. 154(b) by 119 days.

(21) Appl. No.: 11/134,936

(22) Filed: May 23, 2005

(65) Prior Publication Data

US 2005/0267164 A1    Dec. 1, 2005

Related U.S. Application Data

(60) Provisional application No. 60/574,266, filed on May 25, 2004.

(51) Int. Cl.
*A61K 31/4402* (2006.01)
*A61K 31/4439* (2006.01)
*C07D 401/04* (2006.01)

(52) U.S. Cl. ............... 514/341; 544/274.1; 544/274.4
(58) Field of Classification Search ........... 546/274.4, 546/274.1; 514/341
See application file for complete search history.

(56) References Cited

U.S. PATENT DOCUMENTS

| 4,886,817 A | 12/1989 | Takeda et al. ........... 514/341 |
| 5,464,848 A | 11/1995 | Diana ..................... 514/364 |
| 5,780,492 A | 7/1998  | Dinsmore et al. ....... 514/397 |
| 6,706,739 B2 * | 3/2004 | Shia et al. ............... 514/341 |

FOREIGN PATENT DOCUMENTS

| JP | 61 053281 | 3/1986 |
| JP | 06 345714 | 12/1994 |
| WO | WO93/04060 | 3/1993 |
| WO | WO97/08150 | 3/1997 |
| WO | WO97/36892 | 10/1997 |

OTHER PUBLICATIONS

Oberste, et al., J. Gen. Virology 2001, 82, 409-416, 409.*
MMWR Weekly, Feb. 17, 2006, 55(06), 153-156.*
Shia et al., "Design Synthesis, and Structure-Activity Relationship of Pyridyl Imidazolidinones: A Novel Class of Potent and Selective Human Enterovirus 71 Inhibitors", pp. 1644-1655 Mar. 13, 2002 Published on web.

* cited by examiner

*Primary Examiner*—Kamal A. Saeed
*Assistant Examiner*—Michael Barker
(74) *Attorney, Agent, or Firm*—Occhivti Rohlicek & Tsao

(57) ABSTRACT

Compounds of the following formula:

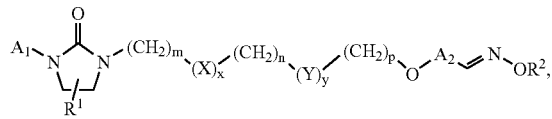

in which $R^1$, $R^2$, $A_1$, $A_2$, X, Y, m, n, p, x and y are as defined herein. Also disclosed are pharmaceutical compositions each containing one or more of these compounds, and use thereof in treating enteroviral infection.

17 Claims, No Drawings

IMIDAZOLIDINONE COMPOUNDS

RELATED APPLICATIONS

This application claims priority to U.S. Provisional Application No. 60/574,266, filed on May 25, 2004, the contents of which are incorporated herein by reference.

BACKGROUND

Enteroviruses, members of the Picornaviridae family, are a group of single-stranded RNA viruses. They reproduce initially in the gastrointestinal tract, which usually does not result in intestinal symptoms. Rather, they cause diseases only after migrating to other organs, such as the nervous system, heart, and lung.

Examples of enteroviruses include coxsackievirus, echovirus, and poliovirus. Clinical manifestations of enteroviral infection include summer grippe (i.e., nonspecific febrile illness), generalized disease of newborns (including myocarditis, low blood pressure, hepatitis, and meningitis), aseptic meningitis encephalitis, pleurodynia (i.e., Bornholm's disease), myocarditis, pericarditis, exanthems, hand-foot-and-mouth disease, herpangina, acute hemorrhagic conjunctivitis, pneumonia and other respiratory diseases, myositis or muscle inflammation, arthritis, and acute kidney inflammation.

SUMMARY

This invention is based on a surprising discovery that a group of imidazolidinone compounds possess anti-enteroviral activity.

One aspect of the present invention relates to compounds of the following formula:

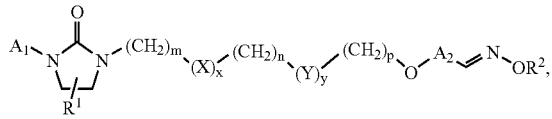

wherein $R^1$ is H, halo, cyano, nitro, alkyl, cycloalkyl, alkoxy, aryl, aralkyl, heterocycloalkyl, or heteroaryl; $R^2$ is H, alkyl, cycloalkyl, aryl, aralkyl, heterocycloalkyl, or heteroaryl; each of $A_1$ and $A_2$, independently, is aryl, aralkyl, or heteroaryl; provided that if $A_1$ is heteroaryl, $A_1$ is attached to the imidazolidinone ring via a C—N bond; each of X and Y, independently, is —(CH$_2$)—, —C(H)(R$^a$), —C(R$^a$)(R$^b$)—, —NR$^c$—, —O—, —S—, —S(O)—, —S(O)$_2$—, aryl, cycloalkyl, heterocycloalkyl, heteroaryl, alkenyl, or alkynyl; each of R$^a$ and R$^b$, independently, being halo, alkyl, hydroxyalkyl, amino, alkoxy, mercapto, thioalkoxy, aryl, aralkyl, or heteroaryl; and R$^c$ being alkyl, aryl, aralkyl, cycloalkyl, heteroaryl, or heterocycloalkyl; each of m, n, and p, independently, is 0, 1, 2, 3, 4, or 5; and each of x and y, independently, is 0 or 1, or a stereoisomer thereof.

Referring to the above formula, one subset of the compounds feature that $A_1$ is 4-pyridyl. In some instances, each of m and x is 0, y is 1, $A_2$ is phenyl, $R^2$ is alkyl, or Y is —(CH$_2$)—, —C(H)(R$^a$)—, or —C(R$^a$)(R$^b$)—, each of R$^a$ and R$^b$ being alkyl (e.g., methyl).

Another subset of the compounds feature that y is 1 and Y is —(CH$_2$)—, —C(H)(CH$_3$)—, or —C(CH$_3$)$_2$—. In some instances, $A_1$ is 4-pyridyl, $A_2$ is phenyl, $R^1$ is H, $R^2$ is alkyl, n is 2, or p is 2.

The term "halo" refers to any radical of fluorine, chlorine, bromine or iodine.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl radical. The term "hydroxyalkyl" refers to alkyl substituted with one or more hydroxy groups. The term "thioalkoxy" refers to a —S-alkyl radical.

The term "alkenyl" refers to a straight or branched hydrocarbon having one or more carbon-carbon double bonds. The term "alkynyl" refers to a straight or branched hydrocarbon having one or more carbon-carbon triple bonds.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, phenylene, naphthyl, and anthracenyl.

The term "cycloalkyl" refers to a saturated and partially unsaturated cyclic hydrocarbon group having 3 to 12 carbons, preferably 3 to 8 carbons, and more preferably 3 to 6 carbons, wherein the cycloalkyl group may be optionally substituted. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocycloalkyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkyl groups include piperazinyl, pyrrolidinyl, dioxanyl, morpholinyl, tetrahydrofuranyl, and the like.

Alkyl, aryl, cycloalkyl, heterocycloalkyl, heteroaryl, alkenyl, and alkynyl mentioned herein include mono-radical and di-radical moieties. For example, alkyl may include alkylene, aryl may include phenylene, alkenyl may include alkylene, and alkynyl may include alkynylene.

Alkyl, hydroxyalkyl, thioalkoxy, alkoxy, alkenyl, alkynyl, aryl, cycloalkyl, heteroaryl, and heterocycloalkyl include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, heterocycloalkyl, in which the alkyl, alkenyl, alkynyl, alkyloxy, aryl, heteroaryl cycloalkyl, and heterocycloalkyl may further substituted.

The compounds described above include their pharmaceutically acceptable salts and prodrugs, if applicable. For example, a salt can be formed between a positively charged ionic group in an imidazolidinone compound (e.g., ammonium) and a negatively charged counterion (e.g., chloride, bromide, or iodide). Examples of prodrugs include esters and other pharmaceutically acceptable compounds, which, upon administration to a subject, are each capable of providing one of the imidazolidinone compounds described above.

Shown below are exemplary compounds of this invention:

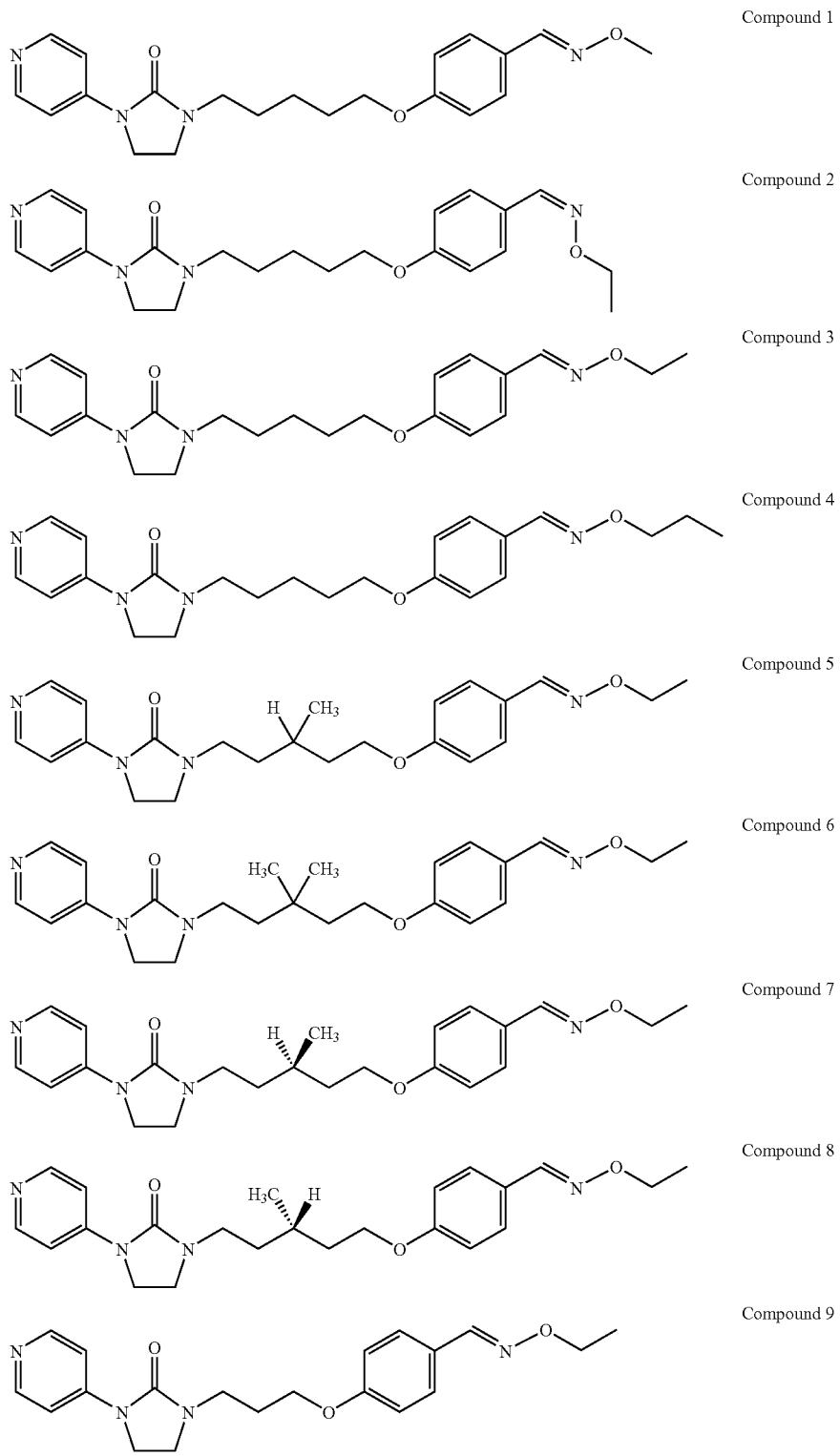

-continued
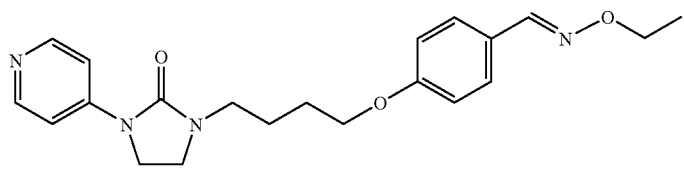
Compound 10
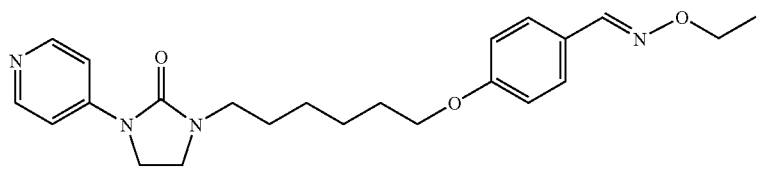
Compound 11
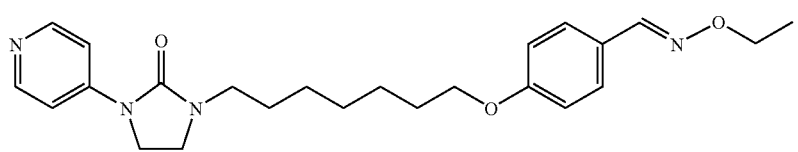
Compound 12
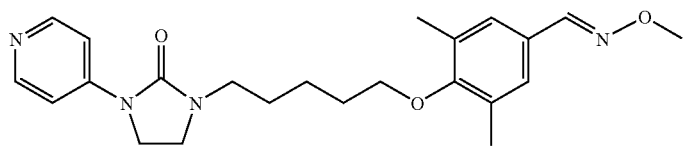
Compound 13
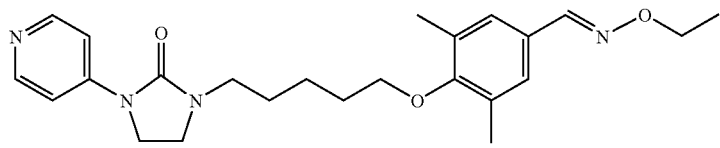
Compound 14
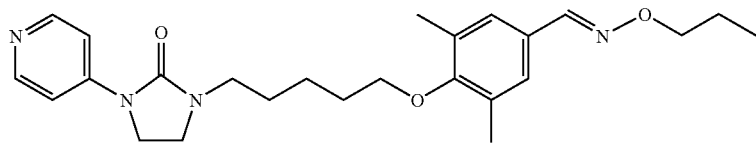
Compound 15
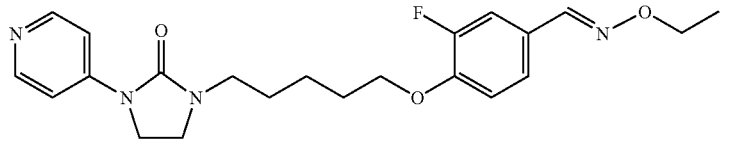
Compound 16
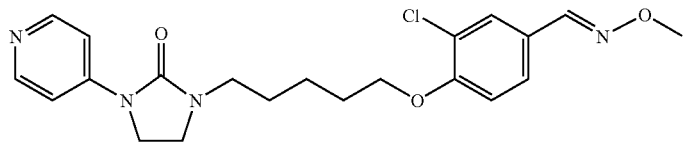
Compound 17
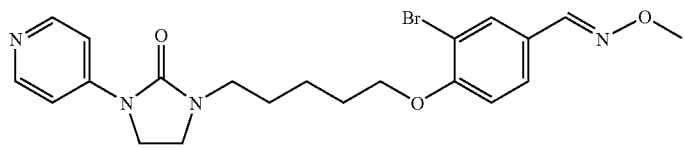
Compound 18
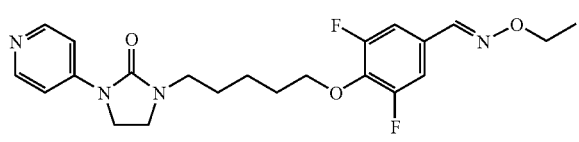
Compound 19

-continued

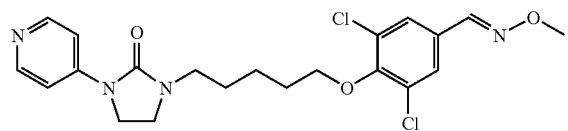

Compound 20

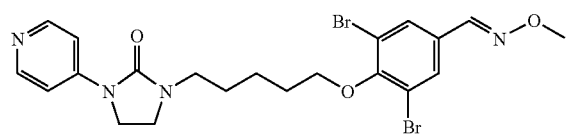

Compound 21

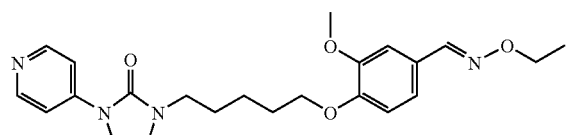

Compound 22

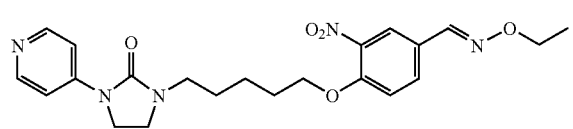

Compound 23

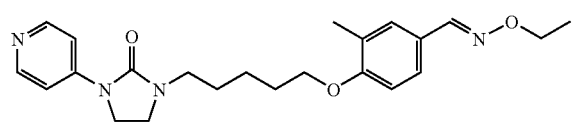

Compound 24

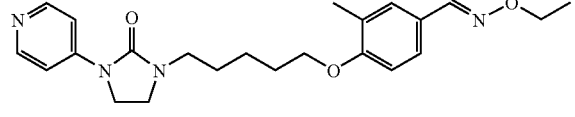

Compound 25

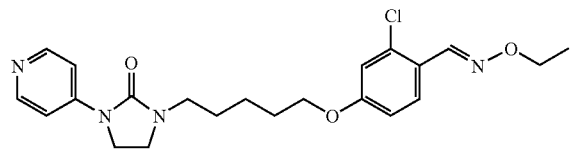

Compound 25

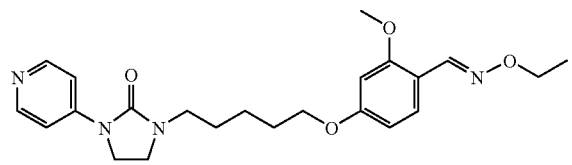

Compound 27

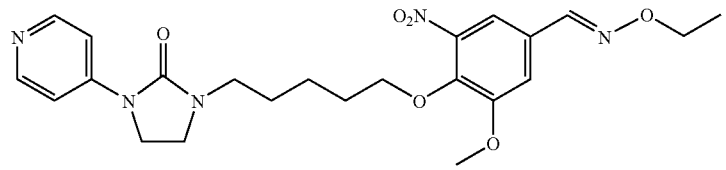

The compounds of this invention can be used as antiviral agents, particularly against human enterovirus. Accordingly, another aspect of this invention relates to a method of treating enteroviral infection by administering to a subject in need thereof an effective amount of one or more of the above-described imidazolidinone compounds.

Also within the scope of this invention is a composition containing one or more of the imidazolidinone compounds described above and a pharmaceutically acceptable carrier for use in treating enteroviral infection, as well as the use of such a composition for the manufacture of a medicament for treating enteroviral infection.

The details of many embodiments of the invention are set forth in the description below. Other features, objects, and advantages of the invention will be apparent from the description and the claims.

DETAILED DESCRIPTION

The imidazolidinone compounds of this invention can be prepared according to methods well known in the art, as well as by the synthetic method disclosed herein.

Scheme I shown below depicts a 2-step synthetic route to a number of the imidazolidinone compounds of this invention.

Scheme 1

Step 1

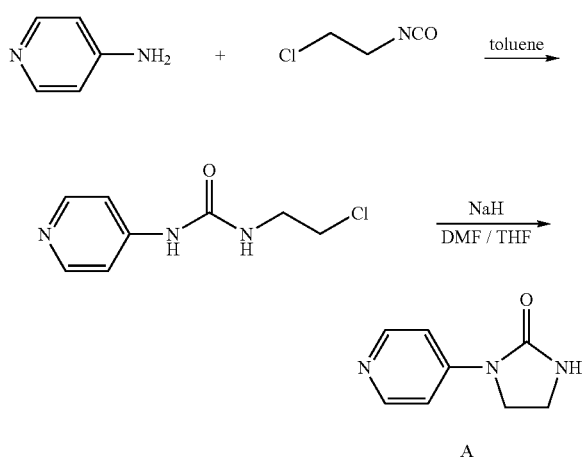

Step 2

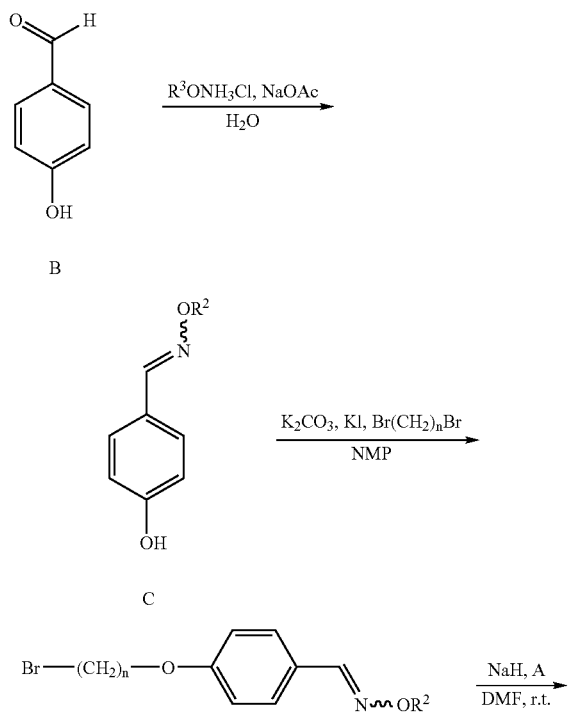

-continued

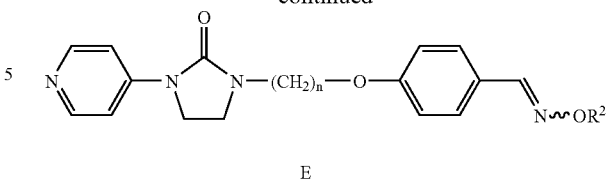

E

In Step 1, 4-aminopyridine is coupled with 2-chloroethylisocyanate to give a urea intermediate. Subsequent intramolecular cyclization of the intermediate provides cyclic urea A in a quantitative yield. In Step 2, coupling benzaldehyde B with O-substituted hydroxylamine hydrochloride affords compound C. See Ley et al., Bioorganic & Medicinal Chemistry, 2001, 9:1879-1885. Compound C is then reacted with dibromoalkane in the presence of sodium carbonate to give compound D, which is treated with cyclic urea A and sodium hydride to afford imidazolidinone compound E.

The chemicals used in the above-described synthetic route may include, for example, solvents, reagents, catalysts, and protecting group and deprotecting group reagents. The method described above may also include steps, either before or after the steps described specifically herein, in order to ultimately allow synthesis of desired imidazolidinone compounds. In addition, various synthetic steps may be performed in an alternate sequence to give the desired compounds. Synthetic chemistry transformations and protecting group methodologies (protection and deprotection) useful in synthesizing applicable imidazolidinone compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Imidazolidinone compounds thus obtained can be further purified by column chromatography, high performance liquid chromatography, or crystallization.

Each of the imidazolidinone compounds described above contains one or more non-aromatic double bond. It may also contain one or more one or more asymmetric centers. Thus, they occur as various stereoisomers, such as racemates and racemic mixtures, single enantiomers, individual diastereomers, diastereomeric mixtures, or cis- or trans- isomeric forms. All such isomeric forms are contemplated.

Imidazolidinone compounds possess anti-enteroviral activity. Thus, this invention also features a method for treating enteroviral infection by administering an effective amount of one or more imidazolidinone compounds to a patient infected by enterovirus. The term "an effective amount" refers to the amount of the imidazolidinone compound(s) required to confer therapeutic effect on the treated subject. The effective amount varies, as recognized by those skilled in the art, depending on the types of diseases treated, route of administration, excipient usage, and the possibility of co-usage with other therapeutic treatment. The term "treating" refers to administering the imidazolidinone compound(s) to a subject who is infected by enterovirus, or has a symptom of the infection, or has a predisposition toward the infection, with the purpose to cure, heal, alleviate, relieve, alter, remedy, ameliorate, improve, or affect the infection, the symptoms of the infection, or the predisposition toward the infection.

To practice the method of the present invention, a composition having one or more of the above-described imidazolidinone compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active imidazolidinone compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active imidazolidinone compound. Examples of other carriers include colloidal silicon oxide, magnesium stearate, cellulose, sodium lauryl sulfate, and D&C Yellow # 10.

The imidazolidinone compounds of this invention can be preliminarily screened by an in vitro inhibition assay (e.g., plaque reduction assay) for their activity against viruses, and particularly, enterovirus. Compounds that demonstrates high activity in the preliminary screening can be further evaluated by in vivo methods well known in the art (see, e.g., Daniel C. Pevear et al., *Antimicrobial Agents & Chemotherapy*, 1999, 43(9): 2109-2115).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Compound 1: 4-[5-(2-oxo-3-pyridin-4-yl-imidazolidin-1-yl)-pentyloxy]-benzaldehyde O-methyl-oxime

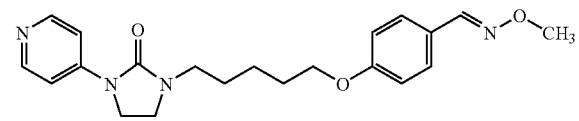

Sodium hydride (60% dispersion in mineral oil, 0.09 g, 2.43 mmol) was added to a solution of 1-(4-pyridyl)-2-imidazolidinone (0.52 g, 3.16 mmol) in anhydrous N,N-dimethyl formamide (3 mL) at 0° C. Then the reaction temperature was allowed to rise to room temperature and the reaction mixture was stirred for 30 min. A solution of 4-(5-bromopentyloxy)-benzaldehyde O-alkyl-oxime (0.73 g, 2.43 mmol) in anhydrous N,N-dimethyl formamide (4 mL) was added. After being stirred at room temperature for 8 hr, the reaction mixture was quenched with cold distilled water (20 mL), and extracted with ethyl ether (30 mL×8). The organic layer was dried over magnesium sulfate and filtered, and the filtrate was evaporated under reduced pressure to yield a crude product. The crude product was purified by column chromatography (1:1 $CH_2Cl_2$/MeOH) and recrystallized in acetonitrile to give Compound 1 (0.79 g, 85%). Analytical data for Compound 1: $^1$H NMR ($CDCl_3$), δ (ppm): 8.43 (d, J=6.3 Hz, 2H), 7.99 (s, 1H), 7.45-7.50 (m, 4H), 6.85 (d, J=8.7 Hz, 2H), 3.98 (t, J=6.3 Hz, 2H), 3.94 (s, 3H), 3.78-3.83 (m, 2H), 3.51-3.56 (m, 2H), 3.34 (t, J=7.0 Hz, 2H), 1.80-1.87 (m, 2H), 1.50-1.66 (m, 4H); MS(ES): m/z 383 (M+H).

EXAMPLES 2-27

Compounds 2-27 were prepared in a manner similar to that described in Example 1. Note that compound 2 was isolated as a cis-isomer and the others were isolated as trans-isomers.

Compound 2: 4-[5-(2-oxo-3-pyridin-4-yl-imidazolidin-1-yl)-pentyloxy]-benzaldehyde O-ethyl-oxime

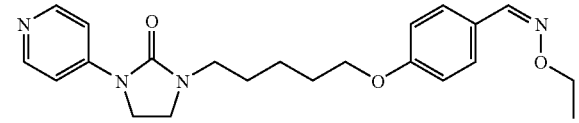

$^1$H NMR ($CDCl_3$), δ (ppm): 8.42 (d, J=6.0 Hz, 2H), 7.99 (s, 1H), 7.44-7.50 (m, 4H), 6.84 (d, J=6.9 Hz, 2H), 4.18 (q, J=7.1 Hz, 2H), 3.96 (t, J=6.3 Hz, 2H), 3.77-3.82 (m, 2H), 3.50-3.55 (m, 2H), 3.33 (t, J=7.1 Hz, 2H), 1.79-1.88 (m, 2H), 1.49-1.67 (m, 4H), 1.30 (t, J=7.1 Hz, 3H). MS(ES): m/z 397 (M+H).

Compound 3: 4-[5-(2-oxo-3-pyridin-4-yl-imidazolidin-1-yl)-pentyloxy]-benzaldehyde O-ethyl-oxime

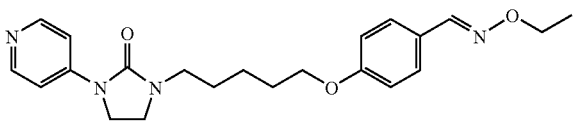

¹H NMR (CDCl₃), δ (ppm): 8.44 (br, 2H), 7.83 (d, J=9.0 Hz, 2H), 7.52 (br, 2H), 7.18 (s, 1H), 6.86 (d, J=6.9 Hz, 2H), 4.22 (q, J=7.2 Hz, 2H), 3.98 (t, J=6.3 Hz, 2H), 3.78-3.84 (m, 2H), 3.51-3.57 (m, 2H), 3.34 (t, J=6.9 Hz, 2H), 1.79-1.89 (m, 2H), 1.47-1.72 (m, 4H). MS(ES): m/z 397 (M+H).

Compound 4: 4-[5-(2-oxo-3-pyridin-4-yl-imidazolidin-1-yl)-pentyloxy]-benzaldehyde O-propyl-oxime

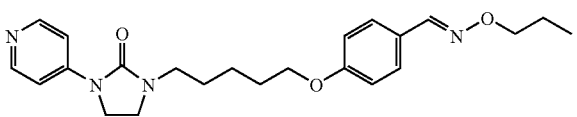

¹H NMR (CDCl₃), δ (ppm): 8.41 (d, J=6.3 Hz, 2H), 7.99 (s, 1H), 7.44-7.48 (m, 4H), 6.83 (d, 8.7 Hz, 4.07 (t, J=6.8 Hz, 2H), 3.96 (t, J=6.3 Hz, 2H), 3.76-3.81 (m, 2H), 3.49-3.54 (m, 2H), 3.32 (t, J=7.1 Hz, 2H), 1.78-1.87 (m, 2H), 1.71 (q, J=7.2 Hz, 2H), 1.46-1.67 (m, 4H), 0.96 (t, J=7.4 Hz, 3H). MS(ES): m/z 411 (M+H).

Compound 5: 4-[3-methyl-5-(2-oxo-3-pyridin-4-yl-imidazolidin-1-yl)-pentyloxy]-benzaldehyde O-ethyl-oxime

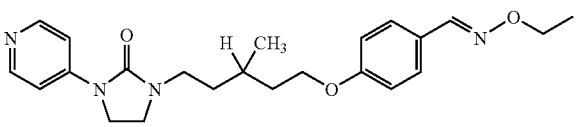

¹H NMR (CDCl₃), δ (ppm): 8.41 (brs, 2H), 7.98 (s, 1H), 7.47-7.44 (m, 4H), 6.83 (d, J=8.7 Hz, 2H), 4.18 (q, J=7.2 Hz, 2H), 4.03-3.97 (m, 2H), 3.79-3.73 (m, 2H), 3.52-3.40 (m, 2H), 3.38-3.29 (m, 2H), 1.86-1.62 (m, 4H), 1.46-1.40 (m, 1H), 1.30 (t, J=7.2 Hz, 3H), 1.02 (d, J=6.3 Hz, 3H). MS(ES): m/z 411 (M+H).

Compound 6: 4-[3,3-dimethyl-5-(2-oxo-3-pyridin-4-yl-imidazolidin-1-yl)-pentyloxy]-benzaldehyde O-ethyl-oxime

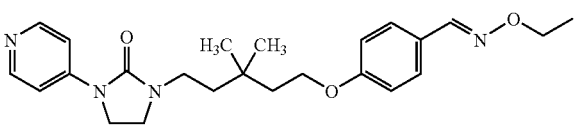

MS(ES): m/z 425 (M+H).

Compound 7: 4-[(R)-3-methyl-5-(2-oxo-3-pyridin-4-yl-imidazolidin-1-yl)-pentyloxy]-benzaldehyde O-ethyl-oxime

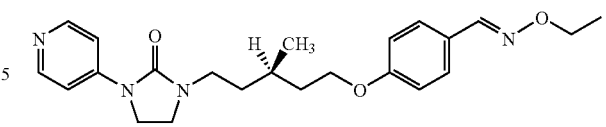

¹H NMR (CDCl₃), δ (ppm): 8.41 (brs, 2H), 7.98 (s, 1H), 7.47-7.44 (m, 4H), 6.83 (d, J=8.7 Hz, 2H), 4.18 (q, J=7.2 Hz, 2H), 4.03-3.97 (m, 2H), 3.79-3.73 (m, 2H), 3.52-3.40 (m, 2H), 3.38-3.29 (m, 2H), 1.86-1.62 (m, 4H), 1.46-1.40 (m, 1H), 1.30 (t, J=7.2 Hz, 3H), 1.02 (d, J=6.3 Hz, 3H). MS(ES): m/z 411 (M+H).

Compound 8: 4-[(S)-3-methyl-5-(2-oxo-3-pyridin-4-yl-imidazolidin-1-yl)-pentyloxy]-benzaldehyde O-ethyl-oxime

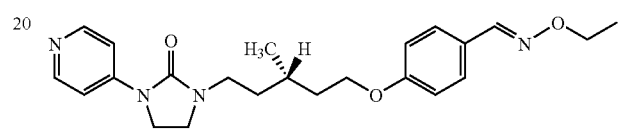

¹H NMR (CDCl₃), δ (ppm): 8.41 (brs, 2H), 7.98 (s, 1H), 7.47-7.44 (m, 4H), 6.83 (d, J=8.7 Hz, 2H), 4.18 (q, J=7.2 Hz, 2H), 4.03-3.97 (m, 2H), 3.79-3.73 (m, 2H), 3.52-3.40 (m, 2H), 3.38-3.29 (m, 2H), 1.86-1.62 (m, 4H), 1.46-1.40 (m, 1H), 1.30 (t, J=7.2 Hz, 3H), 1.02 (d, J=6.3 Hz, 3H); MS(ES): m/z 411 (M+H).

Compounds 9: 4-[3-(2-oxo-3-pyridin-4-yl-imidazolidin-1-yl)-propoxy]-benzaldehyde O-ethyl-oxime

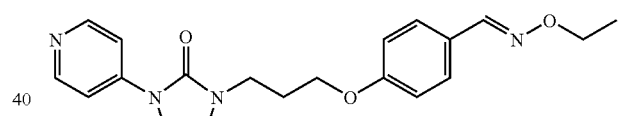

Compound 9 was prepared in a similar manner as described in Compound 1.

¹H NMR (CDCl₃), δ (ppm): 8.42 (d, J=5.7 Hz, 2H), 7.99 (s, 1H), 7.43-7.49 (m, 4H), 6.85 (d, J=8.7 Hz, 2H), 4.18 (q, J=7.2 Hz, 2H), 4.04 (t, J=6.2 Hz, 2H), 3.80 (t, J=8.1 Hz, 2H), 3.49-3.60 (m, 4H), 2.08 (m, 2H), 1.30 (t, J=7.1 Hz, 3H); MS(ES): m/z 369 (M+H).

Compound 10: Synthesis of 4-[4-(2-oxo-3-pyridin-4-yl-imidazolidin-1-yl)-butoxy]-benzaldehyde O-ethyl-oxime

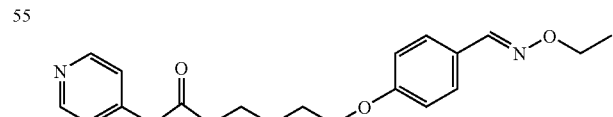

¹H NMR (CDCl₃), δ (ppm): 8.42 (dd, J=6.6, 1.7 Hz, 2H), 7.98 (s, 1H), 7.43-7.48 (m, 4H), 6.84 (dd, J=8.7, 2.0 Hz, 2H), 4.18 (q, J=7.1 Hz, 2H), 4.00 (t, J=5.7 Hz, 2H), 3.74-3.80 (m, 2H), 3.51-3.56 (m, 2H), 3.38 (t, J=6.9 Hz, 2H), 1.76-1.84 (m, 4H), 1.30 (t, J=6.9 Hz, 3H); MS(ES): m/z 383 (M+H).

Compound 11: 4-[6-(2-oxo-3-pyridin-4-yl-imidazolidin-1-yl)-hexyloxy]-benzaldehyde O-ethyl-oxime

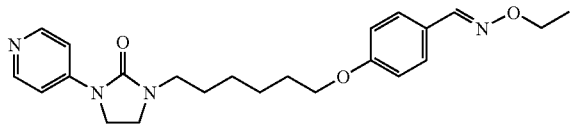

¹H NMR (CDCl₃), δ (ppm): 8.42 (dd, J=6.3, 1.2 Hz, 2H), 7.99 (s, 1H), 7.44-7.49 (m, 4H), 6.84 (d, J=8.7 Hz, 2H), 4.18 (q, J=6.9 Hz, 2H), 3.96 (t, J=6.3 Hz, 2H), 3.76-3.82 (m, 2H), 3.52-3.55 (m, 2H), 3.31 (t, J=6.9 Hz, 2H), 1.74-1.84 (m, 2H), 1.37-1.62 (m, 6H), 1.30 (t, J=7.1 Hz, 3H); MS(ES): m/z 411 (M+H).

Compound 12: 4-[7-(2-oxo-3-pyridin-4-yl-imidazolidin-1-yl)-heptyloxy]-benzaldehyde O-ethyl-oxime

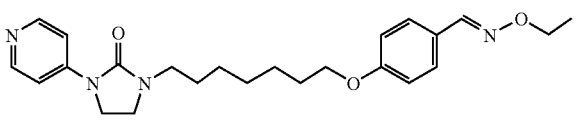

¹H NMR (CDCl₃), δ (ppm): 8.41 (dd, J=6.6, 1.5 Hz, 2H), 7.99 (s, 1H), 7.44-7.49 (m, 4H), 6.84 (d, J=8.7 Hz, 2H), 4.18 (q, J=6.9 Hz, 2H), 3.95 (t, J=6.8 Hz, 2H), 3.76-3.81 (m, 2H), 3.48-3.54 (m, 2H), 3.29 (t, J=7.4 Hz, 2H), 1.75-1.83 (m, 2H), 1.37-1.63 (m, 8H), 1.30 (t, J=7.1 Hz, 3H); MS(ES): m/z 425 (M+H).

Compound 13: 3,5-dimethyl-4-[5-(2-oxo-3-pyridin-4-yl-imidazolidin-1-yl)-pentyloxy]-benzaldehyde O-methyl-oxime

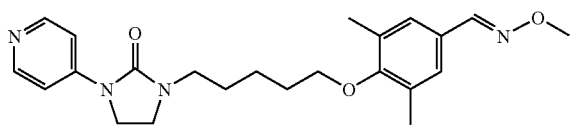

¹H NMR (CDCl₃) δ (ppm): 8.42 (d, J=6.0 Hz, 2H), 7.93 (s, 1H), 7.46 (d, J=6.3 Hz, 2H), 7.21 (s, 2H), 3.93 (s, 3H), 3.81 (dd, J=9.6 Hz, J=6.6 Hz, 2H), 3.76 (t, J=7.1 Hz, 2H), 3.54 (dd, J=9.6 Hz, J=6.3 Hz, 2H) 3.35 (t, J=7.1 Hz, 2H), 2.25 (s, 6H), 1.89-1.80 (m, 2H), 1.72-1.54 (m. 4H); MS(ES): m/z 411 (M+H).

Compound 14: 3,5-dimethyl-4-[5-(2-oxo-3-pyridin-4-yl-imidazolidin-1-yl)-pentyloxy]-benzaldehyde O-ethyl-oxime

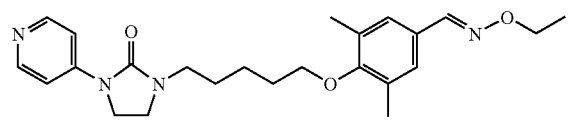

¹H NMR (CDCl₃) δ (ppm): 8.42 (d, J=5.1 Hz, 2H), 7.94 (s, 1H), 7.49 (d, J=6.3 Hz, 2H), 7.21 (s, 2H), 4.18 (q, J=7.1 Hz, 2H), 3.82 (dd, J=9.6 Hz, J=6.6 Hz, 2H), 3.75 (t, J=6.3 Hz, 2H), 3.55 (dd, J=9.6 Hz, J=6.3 Hz, 2H), 3.35 (t, J=7.2 Hz, 2H), 2.25 (s, 6H), 1.89-1.80 (m, 2H), 1.70-1.54 (m. 4H), 1.30 (t, J=7.1 Hz, 3H); MS(ES): m/z 425 (M+H).

Compound 15: 3,5-dimethyl-4-[5-(2-oxo-3-pyridin-4-yl-imidazolidin-1-yl)-pentyloxy]-benzaldehyde O-propyl-oxime

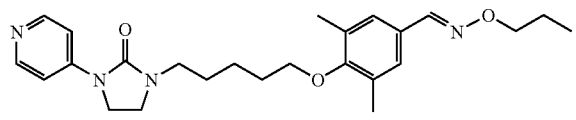

¹H NMR (CDCl₃) δ (ppm): 8.43 (dd, J=6.0 Hz, J=1.5 Hz, 2H), 7.95 (s, 1H), 7.49 (dd, J=4.8 Hz, J=1.5 Hz, 2H), 7.20 (s, 2H), 4.08 (t, J=6.8 Hz, 2H), 3.81 (dd, J=9.8 Hz, J=6.5 Hz, 2H), 3.75 (t, J=6.5 Hz, 2H), 3.54 (dd, J=9.6 Hz, J=6.3 Hz, 2H), 3.35 (t, J=6.9 Hz, 2H), 2.25 (s, 6H), 1.89-1.80 (m, 2H), 1.78-1.52 (m. 6H), 0.96 (t, J=7.4 Hz, 3H). MS(ES): m/z 439 (M+H).

Compound 16: 3-fluoro-4-[5-(2-oxo-3-pyridin-4-yl-imidazolidin-1-yl)-pentyloxy]-benzaldehyde O-ethyl-oxime

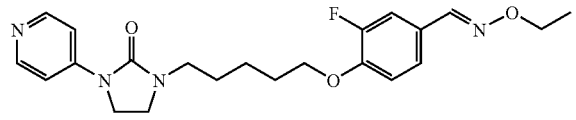

¹H NMR (CDCl₃) δ (ppm): 8.38 (dd, J=5.4 Hz, J=0.9 Hz, 2H), 7.91 (s, 1H), 7.42 (dd, J=5.1 Hz, J=1.2 Hz, 2H), 7.34 (dd, J=12 Hz, J=1.5 Hz, 1H), 7.13 (d, J=8.1 Hz, 1H), 6.86 (d, J=8.3 Hz, 1H), 4.16 (q, J=7.0 Hz, 2H), 4.00 (t, J=6.2 Hz, 2H), 3.76 (t, J=7.8 Hz, 2H), 3.49 (t, J=8.0 Hz, 2H), 3.30 (t, J=7.1 Hz, 2H), 1.89-1.80 (m, 2H), 1.67-1.46 (m. 4H), 1.28 (t, J=7.2 Hz, 3H); MS(ES): m/z 415 (M+H).

Compound 17: 3-chloro-4-[5-(2-oxo-3-pyridin-4-yl-imidazolidin-1-yl)-pentyloxy]-benzaldehyde O-methyl-oxime

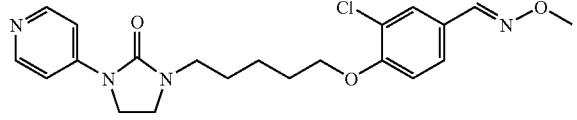

¹H NMR (CDCl₃) δ (ppm): 8.41 (dd, J=5.1 Hz, J=1.5 Hz, 2H), 7.92 (s, 1H), 7.61 (d, J=2.1 Hz, 1H), 7.45 (dd, J=5.0 Hz, J=1.7 Hz, 2H), 7.34 (dd, J=8.6 Hz, J=2.0 Hz, 1H), 6.85 (d, J=8.4 Hz, 1H), 4.18 (q, J=7.1 Hz, 2H), 4.03 (t, J=6.3 Hz, 2H), 3.79 (dd, J=9.8 Hz, J=6.2 Hz, 2H), 3.53 (dd, J=9.6 Hz, J=6.6 Hz, 2H), 3.34 (t, J=6.9 Hz, 2H), 1.91-1.87 (m, 2H), 1.69-1.53 (m, 4H), 1.30 (t, J=7.1 Hz, 3H); MS(ES); m/z 431 (M+H).

Compound 18: 3-bromo-4-[5-(2-oxo-3-pyridin-4-yl-imidazolidin-1-yl)-pentyloxy]-benzaldehyde O-methyl-oxime

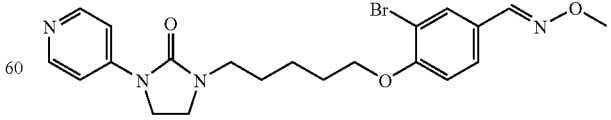

¹H NMR (CDCl₃) δ (ppm): 8.41 (dd, J=5.1 Hz, J=1.5 Hz, 2H), 7.92 (s, 1H), 7.78 (d, J=2.1 Hz, 1H), 7.45 (dd, J=5.0 Hz, J=1.7 Hz, 2H), 7.39 (dd, J=8.4 Hz, J=2.1 Hz, 1H), 6.81 (d, J=8.7 Hz, 1H), 4.18 (q, J=7.0 Hz, 2H), 4.03 (t, J=6.3 Hz, 2H), 3.79 (dd, J=9.8 Hz, J=6.5 Hz, 2H), 3.53 (dd, J=9.6 Hz, J=6.3 Hz, 2H), 3.34 (t, J=6.9 Hz, 2H), 1.91-1.86 (m, 2H), 1.70-1.54 (m, 4H), 1.30 (t, J=7.1 Hz, 3H); MS(ES): m/z 475, 477 (M+H).

Compound 19: 3,5-Difluoro-4-[5-(2-oxo-3-pyridin-4-yl-imidazolidin-1-yl)-pentyloxy]-benzaldehyde O-ethyl-oxime

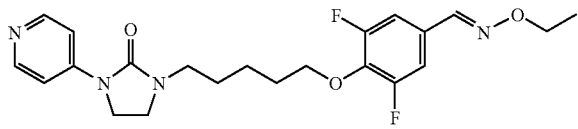

$^1$H NMR (CDCl$_3$) δ (ppm): 8.41 (dd, J=5.1 Hz, J=1.5 Hz, 2H), 7.87 (s, 1H), 7.45 (dd, J=6.3 Hz, J=1.5 Hz, 2H), 7.09 (m, 2H), 4.19 (q, J=7.3 Hz, 2H), 4.15 (t, J=6.3 Hz, 2H), 3.80 (dd, J=9.5 Hz, J=6.5 Hz, 2H), 3.53 (dd, J=9.5 Hz, J=6.8 Hz, 2H), 3.32 (t, J=6.9 Hz, 2H), 1.82-1.75 (m, 2H), 1.69-1.50 (m, 4H), 1.30 (t, J=7.2 Hz, 3H); MS(ES): m/z 433 (M+H).

Compound 20: 3,5-dichloro-4-[5-(2-oxo-3-pyridin-4-yl-imidazolidin-1-yl)-pentyloxy]-benzaldehyde O-methyl-oxime

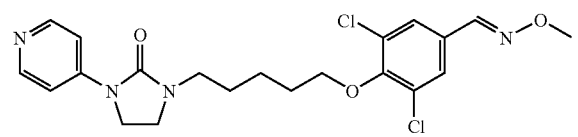

$^1$H NMR (CDCl$_3$) δ (ppm): 8.42 (d, J=6.3 Hz, 2H), 7.87 (s, 1H), 7.48 (s, 2H), 7.45 (dd, J=4.7 Hz, J=1.7 Hz, 2H), 4.20 (q, J=7.0 Hz, 2H), 4.02 (t, J=6.2 Hz, 2H), 3.80 (dd, J=9.9 Hz, J=6.6 Hz, 2H), 3.54 (dd, J=9.8 Hz, J=6.5 Hz, 2H), 3.34 (t, J=7.2 Hz, 2H), 1.93-1.84 (m, 2H), 1.71-1.57 (m, 4H), 1.30 (t, J=7.1 Hz, 3H); MS(ES): m/z 465 (M+H).

Compound 21: 3,5-dibromo-4-[5-(2-oxo-3-pyridin-4-yl-imidazolidin-1-yl)-pentyloxy]-benzaldehyde O-methyl-oxime

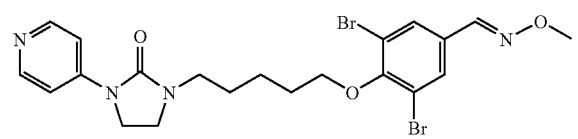

$^1$H NMR (CDCl$_3$) δ (ppm): 8.42 (dd, J=5.0 Hz, J=1.4 Hz, 2H), 7.87 (s, 1H), 7.69 (s, 2H), 7.45 (dd, J=5.1 Hz, J=1.5 Hz, 2H), 4.20 (q, J=7.0 Hz, 2H), 4.00 (t, J=6.2 Hz, 2H), 3.80 (dd, J=9.6 Hz, J=6.6 Hz, 2H), 3.55 (dd, J=9.6 Hz, J=6.3 Hz, 2H), 3.35 (t, J=6.8 Hz, 2H), 1.91-1.76 (m, 2H), 1.72-1.61 (m. 4H), 1.30 (t, J=7.1 Hz, 3H); MS(ES): m/z 555 (M+H).

Compound 22: 3-methoxy-4-[5-(2-oxo-3-pyridin-4-yl-imidazolidin-1-yl)-pentyloxy]-benzaldehyde O-ethyl-oxime

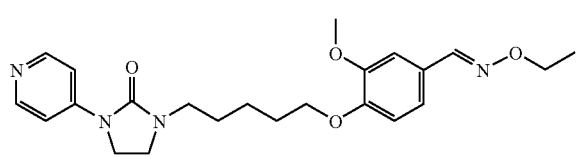

$^1$H NMR (CDCl$_3$) δ (ppm): 8.41 (dd, J=4.8 Hz, J=1.5 Hz, 2H), 7.97 (s, 1H), 7.45 (dd, J=5.0 Hz, J=1.7 Hz, 2H), 7.20 (d, J=1.8 Hz, 1H), 6.95 (dd, J=8.3 Hz, J=2.0 Hz, 1H), 6.80 (d, J=8.1 Hz, 1H), 4.19 (q, J=7.1 Hz, 2H), 4.02 (t, J=6.6 Hz, 2H), 3.87 (s, 3H), 3.78 (dd, J=9.6 Hz, J=6.3 Hz, 2H), 3.52 (dd, J=9.9 Hz, J=7.2 Hz, 2H), 3.32 (t, J=6.9 Hz, 2H), 1.92-1.86 (m, 2H), 1.67-1.49 (m. 4H), 1.31 (t, J=7.1 Hz, 3H); MS(ES): m/z 427 (M+H).

Compound 23: 3-nitro-4-[5-(2-oxo-3-pyridin-4-yl-imidazolidin-1-yl)-pentyloxy]-benzaldehyde O-ethyl-oxime

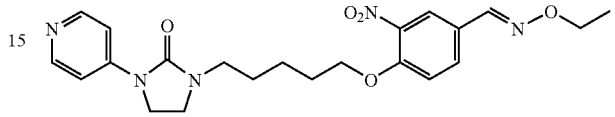

$^1$H NMR (CDCl$_3$) δ (ppm): 8.40 (dd, J=5.0 Hz, J=1.7 Hz, 2H), 7.99 (d, J=2.1 Hz, 1H), 7.96 (s, 1H), 7.68 (dd, J=8.9 Hz, J=2.3 Hz, 1H), 7.44 (dd, J=4.8 Hz, J=1.5 Hz, 2H), 7.01 (d, J=8.7 Hz, 1H), 4.19 (q, J=7.1 Hz, 2H), 4.11 (t, J=6.0 Hz, 2H), 3.81 (dd, J=9.6 Hz, J=6.3 Hz, 2H), 3.54 (dd, J=9.9 Hz, J=6.3 Hz, 2H), 3.33 (t, J=6.9 Hz, 2H), 1.92-1.83 (m, 2H), 1.68-1.52 (m. 4H), 1.30 (t, J=7.1 Hz, 3H); MS(ES): m/z 442 (M+H).

Compound 24: 3-methyl-4-[5-(2-oxo-3-pyridin-4-yl-imidazolidin-1-yl)-pentyloxy]-benzaldehyde O-ethyl-oxime

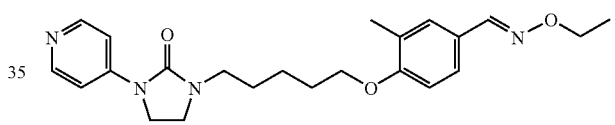

$^1$H NMR (CDCl$_3$) δ (ppm): 8.43 (dd, J=5.1 Hz, J=1.2 Hz, 2H), 7.97 (s, 1H), 7.45 (dd, J=4.8 Hz, J=1.5 Hz, 2H), 7.39 (s, 1H), 7.28 (dd, J=8.4 Hz, J=1.8 Hz, 1H), 6.74 (d, J=8.4 Hz, 1H), 4.18 (q, J=7.0 Hz, 2H), 3.97 (t, J=6.5 Hz, 2H), 3.79 (dd, J=9.6 Hz, J=6.6 Hz, 2H), 3.53 (dd, J=9.6 Hz, J=6.6 Hz, 2H), 3.34 (t, J=6.9 Hz, 2H), 2.19 (s, 3H), 1.88-1.83 (m, 2H), 1.67-1.51 (m. 4H), 1.31 (t, J=7.1 Hz, 3H); MS(ES): m/z 411 (M+H).

Compound 25: 2-chloro-4-[5-(2-oxo-3-pyridin-4-yl-imidazolidin-1-yl)-pentyloxy]-benzaldehyde O-ethyl-oxime

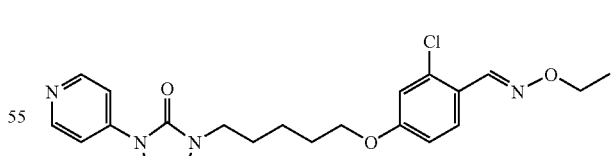

$^1$H NMR (CDCl$_3$) δ (ppm): 8.41 (dd, J=4.8 Hz, J=1.5 Hz, 2H), 8.38 (s, 1H), 7.77 (d, J=9.0 Hz, 1H), 7.44 (dd, J=5.1 Hz, J=1.5 Hz, 2H), 6.83 (d, J=2.4 Hz, 1H), 6.75 (dd, J=8.7 Hz, J=2.4 Hz, 1H), 4.19 (q, J=7.0 Hz, 2H), 3.94 (t, J=6.3 Hz, 2H), 3.78 (dd, J=9.6 Hz, J=6.3 Hz, 2H), 3.52 (dd, J=9.2 Hz, J=6.5 Hz, 2H), 3.32 (t, J=7.1 Hz, 2H), 1.84-1.80 (m, 2H), 1.66-1.50 (m. 4H), 1.30 (t, J=7.1 Hz, 3H); MS(ES): m/z 431 (M+H).

Compound 26: 2-methoxy-4-[5-(2-oxo-3-pyridin-4-yl-imidazolidin-1-yl)-pentyloxy]-benzaldehyde O-ethyl-oxime

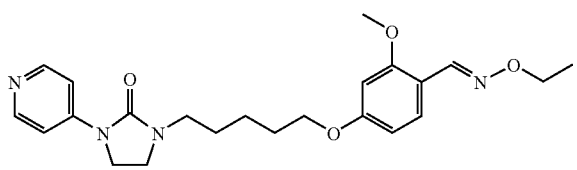

$^1$H NMR (CDCl$_3$) δ (ppm): 8.42 (dd, J=4.8 Hz, J=1.5 Hz, 2H), 8.35 (s, 1H), 7.66 (d, J=8.4 Hz, 1H), 7.45 (dd, J=5.0 Hz, J=1.7 Hz, 2H), 6.44 (dd, J=8.7 Hz, J=2.4 Hz, 1H), 6.39 (d, J=2.4 Hz, 1H), 4.17 (q, J=7.1 Hz, 2H), 3.97 (t, J=6.3 Hz, 2H), 3.80 (dd, J=9.6 Hz, J=6.3 Hz, 2H), 3.78 (s, 3H), 3.53 (dd, J=9.6 Hz, J=6.6 Hz, 2H), 3.33 (t, J=7.2 Hz, 2H), 1.88-1.79 (m, 2H), 1.70-1.49 (m, 4H), 1.30 (t, J=7.2 Hz, 3H); MS(ES): m/z 427 (M+H).

Compound 27: 3-methoxy-5-nitro-4-[5-(2-oxo-3-pyridin-4-yl-imidazolidin-1-yl)-pentyloxy]-benzaldehyde O-ethyl-oxime

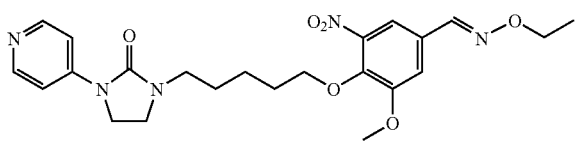

$^1$H NMR (CDCl$_3$) δ (ppm): 8.41 (dd, J=5.0 Hz, J=1.7 Hz, 2H), 7.94 (s, 1H), 7.45 (dd, J=4.8 Hz, J=1.5 Hz, 2H), 7.38 (d, J=2.1 Hz, 1H), 7.35 (d, J=1.8 Hz, 1H), 4.21 (q, J=7.1 Hz, 2H), 4.14 (t, J=5.9 Hz, 2H), 3.91 (s, 3H), 3.81 (dd, J=9.8 Hz, J=6.5 Hz, 2H), 3.55 (dd, J=9.8 Hz, J=6.5 Hz, 2H), 3.33 (t, J=6.9 Hz, 2H), 1.84-1.77 (m, 2H), 1.67-1.48 (m. 4H), 1.31 (t, J=7.1 Hz, 3H); MS(ES): m/z 472 (M+H).

EXAMPLE 28

Enterovirus 71 (EV71) isolates were obtained from Chang Gung Children's Hospitals (Taipei, Taiwan) and National Cheng Kung University Hospital (Tainan, Taiwan). EV71-2231 and EV71-1743 were isolated from throat swabs. EV71-2086 was isolated from the skin lesion of an implicated HFMD (hand, foot, and mouth disease) patient. EV71-4643 was a clinical isolate obtained from the throat swabs of an 18-month-old patient with encephalitis). BrCr, the prototype of EV71, was obtained from the American Type Culture Collection (ATCC Accession No. VR 784). Vero cells (ATCC Accession No. CCL-81) were used for virus isolation and propagation.

The antiviral activity of a number of imidazolidinone compounds was determined by a standard plaque reduction assay as described in Otto et al., Antimicrobial Agents & Chemotherapy, 1985, 27:883-886.

More specifically, vero cells in monolayers were infected at a virus concentration to give approximately 50-100 plaques per monolayer in a virus control (without a test compound). A compound to be tested was serially diluted and included in the agar-medium overlay. Plates were incubated at 35° C. for 96 hours. The plaques were stained with crystal violet and counted. IC$_{50}$, the concentration at which a test compound reduced the number of plaques by 50% with respect to the untreated virus control, was then determined.

Compounds 1-8 were tested against EV71-2231 and EV71-4643. Each test compound showed antiviral activity against EV71-2231 and EV71-4643, i.e., IC$_{50}$ is 38.1 nm or much lower.

Compound 3 was also tested against EV71-2086, EV71-1743, and BrCr. It showed antiviral activity against these three EV71 isolates, i.e., IC$_{50}$ is 9 nm or much lower.

EXAMPLE 29

A mouse-adapted EV71 strain, 4643 MP4, is propagated in rhabdomyosarcoma cells (RD) in DMEM supplemented with 2% fetal bovine serum. The virus titer expressed in a plaque formation unit (PFU) is determined by a plaque assay on RD cells based on typical cytopathic effect. A virus stock with a titer of 1.5×10$^7$ PFU/ml is collected and kept at −80° C. for further animal studies.

Two-day old ICR neonatal mice are intraperitoneally inoculated with EV71 of 435 PFU in 50 μl. Each test compound is suspended in 0.5% methyl-cellulose. The virus-inoculated neonatal mice are each orally treated with a test compound suspension or, as a negative control, the formulation vehicle. Different regimens are explored to investigate antiviral activity of each test compound, i.e., 10 to 200 mg/kg; before and/or after the inoculation; and daily treatments for a week. The mice are examined daily and the mortality of treated and control groups are recorded.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to above-described imidazolidinone compounds also can be made, screened for the above-described activities and used to practice this invention. Thus, other embodiments are also within the claims.

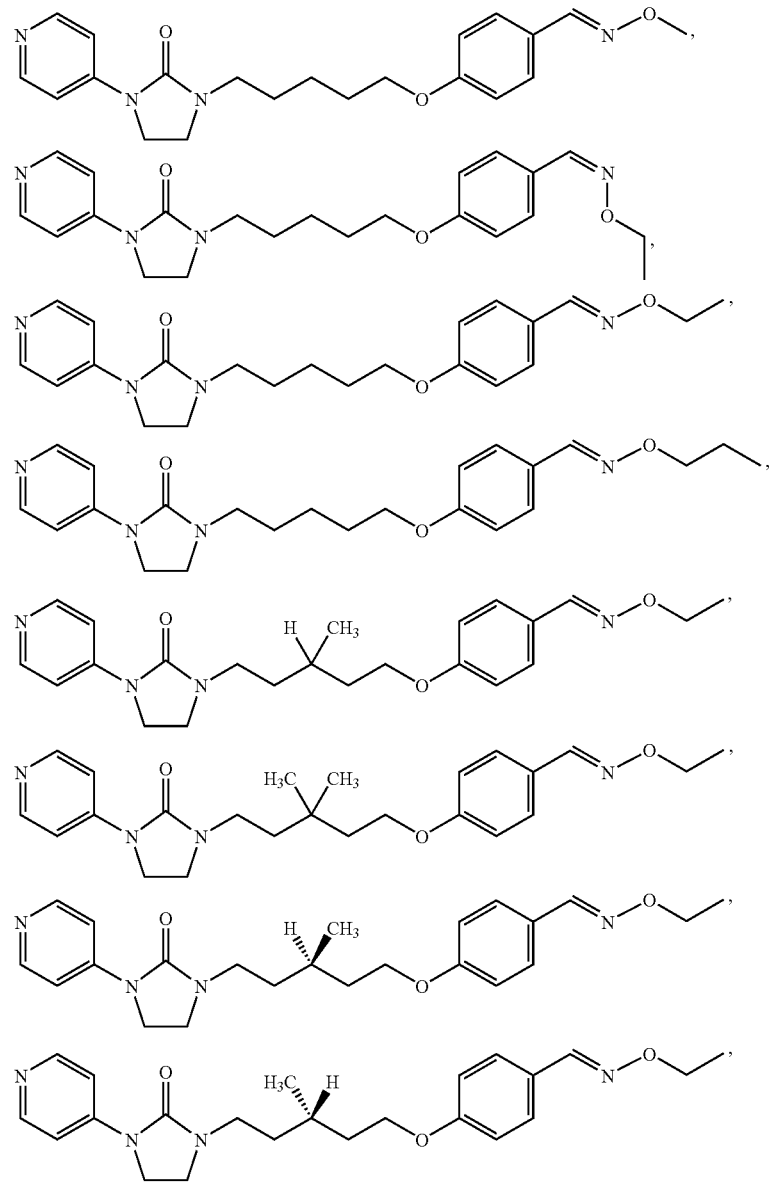

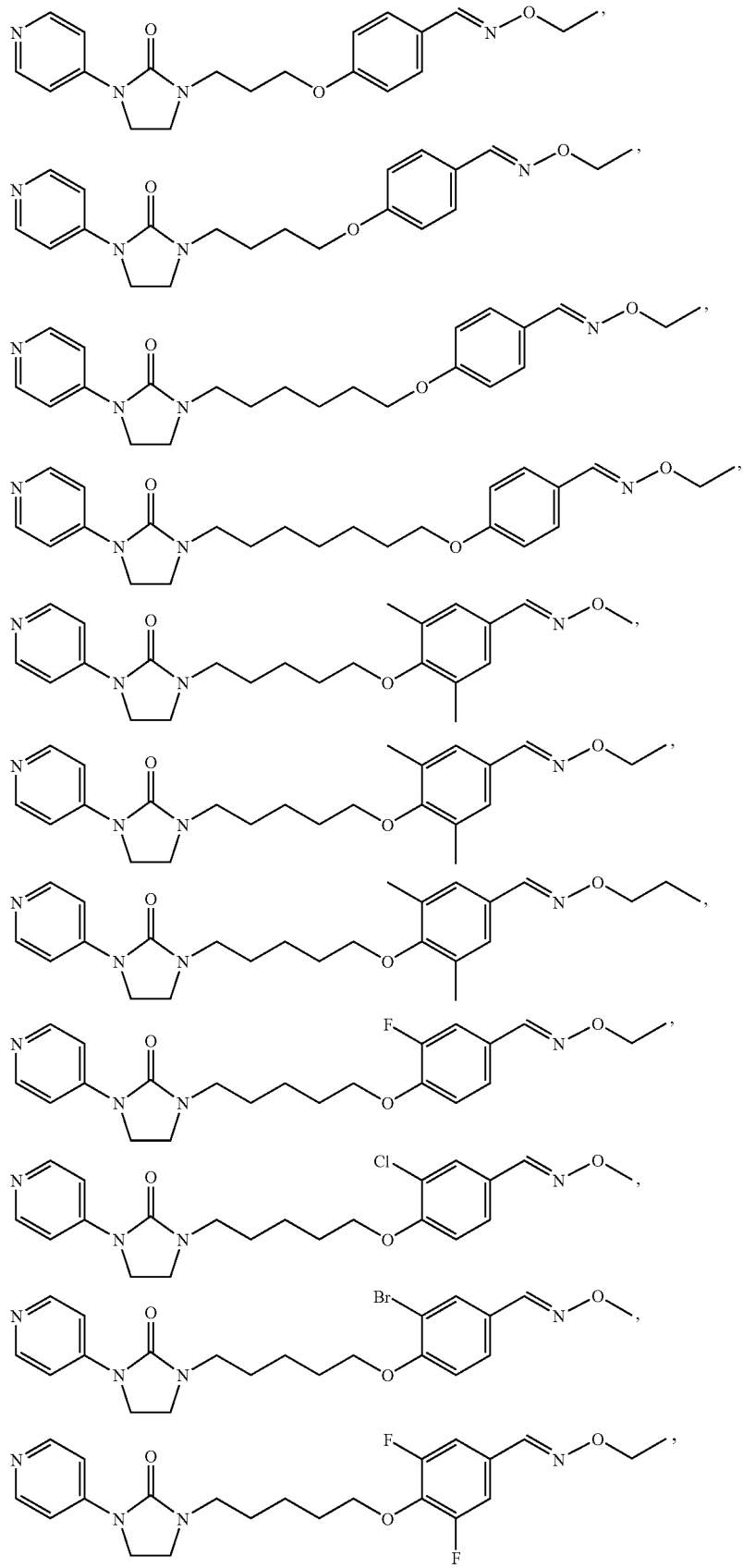

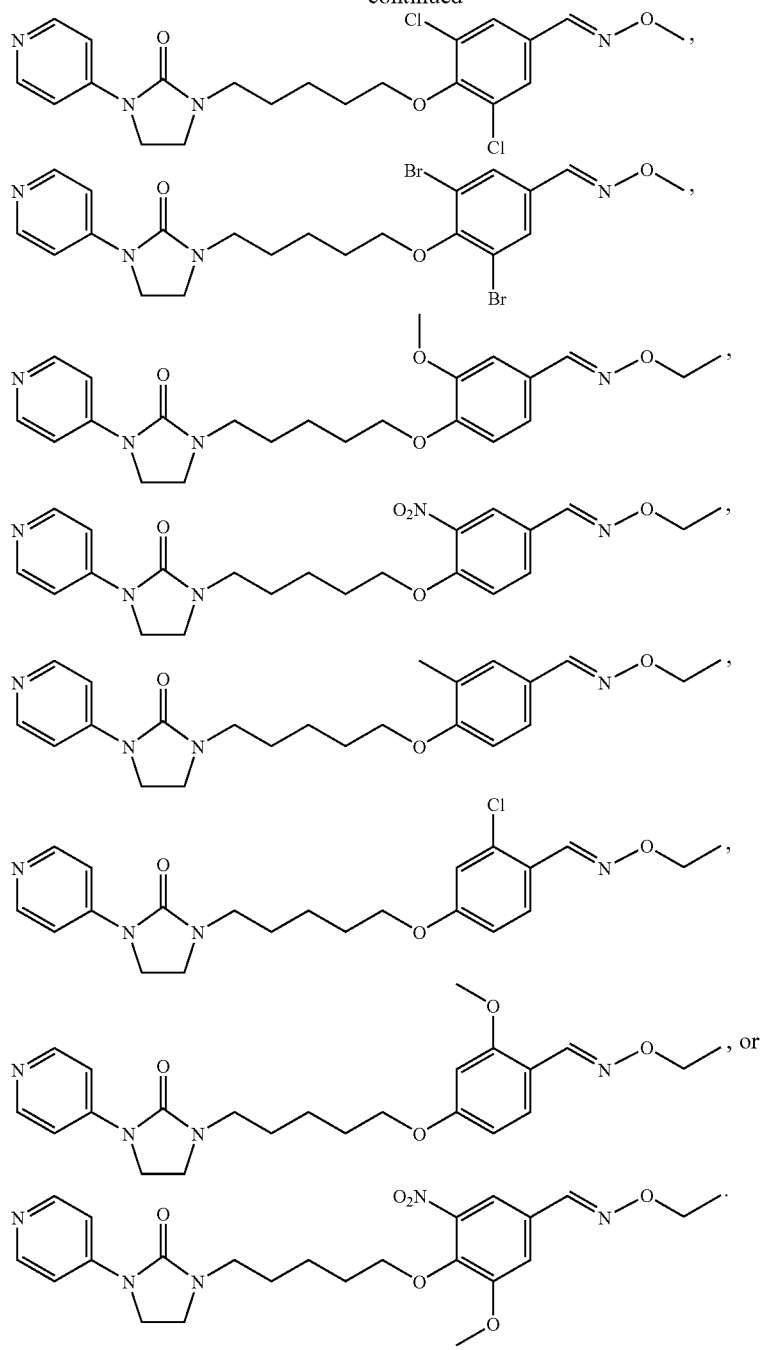

What is claimed is:

1. A compound of the following formula:

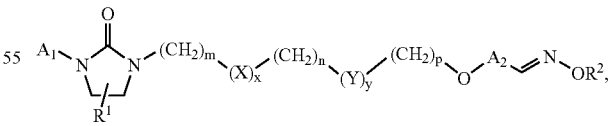

wherein

R$^1$ is H, halo, cyano, nitro, amino, alkyl, cycloalkyl, alkoxy, aryl, aralkyl, heterocycloalkyl, or heteroaryl;

R$^2$ is H, alkyl, cycloalkyl, aryl, aralkyl, heterocycloalkyl, or heteroaryl;

each of A$_1$ and A$_2$, independently, is aryl, aralkyl, or heteroaryl; provided that if A$_1$ is heteroaryl, A$_1$ is attached to the imidazolidinone ring via a C—N bond;

each of X and Y, independently, is —(CH$_2$)—, —C(H)(R$^a$), —C(R$^a$)(R$^b$)—, —NR$^c$—, —O—, —S—, —S(O)—, —S(O)$_2$—, aryl, cycloalkyl, heterocycloalkyl, heteroaryl, alkenyl, or alkynyl;

each of R$^a$ and R$^b$, independently, being halo, amino, alkyl, hydroxyalkyl, alkoxy, mercapto, thioalkoxy, aryl, aralkyl, or heteroaryl; and R$^c$ being alkyl, aryl, aralkyl, cycloalkyl, heteroaryl, or heterocycloalkyl;

each of m, n, and p, independently, is 0, 1, 2, 3, 4, or 5; and each of x and y, independently, is 0 or 1; or a stereoisomer thereof.

2. The compound of claim 1, wherein A$_1$ is 4-pyridyl.

3. The compound of claim 2, wherein each of m and x is 0.

4. The compound of claim 3, wherein y is 1, and Y is —(CH$_2$)—.

5. The compound of claim 3, wherein y is 1, and Y is —C(H)(R$^a$)— or —C(R$^a$)(R$^b$)—, each of R$^a$ and R$^b$ being alkyl.

6. The compound of claim 3, wherein A$_2$ is phenyl.

7. The compound of claim 1, wherein y is 1 and Y is —(CH$_2$)—, —C(H)(CH$_3$)— or —C(CH$_3$)$_2$—.

8. The compound of claim 7, wherein A$_1$ is 4-pyridyl and A$_2$ is phenyl.

9. The compound of claim 8, wherein R$^2$ is alkyl.

10. The compound of claim 9, wherein each of n and p is 2.

11. The compound of claim 10, wherein R$^1$ is H.

12. The compound of claim 1, wherein the compound is

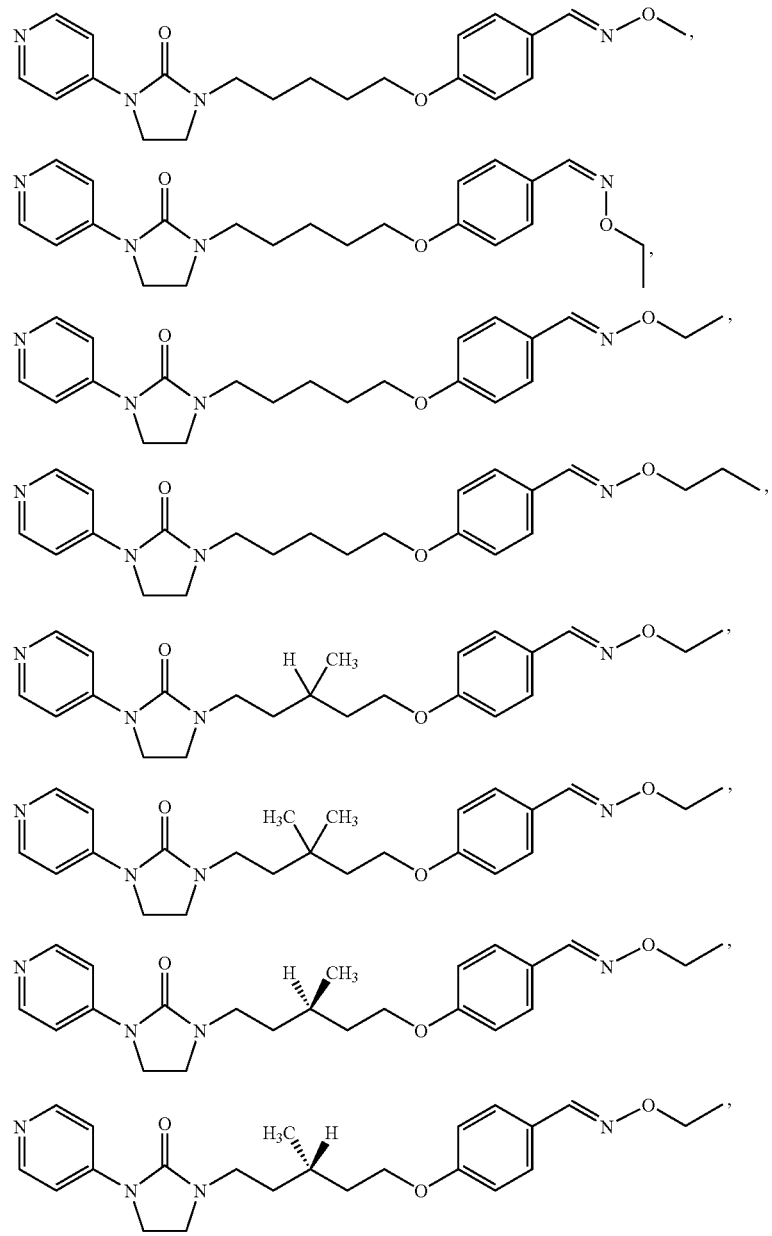

-continued
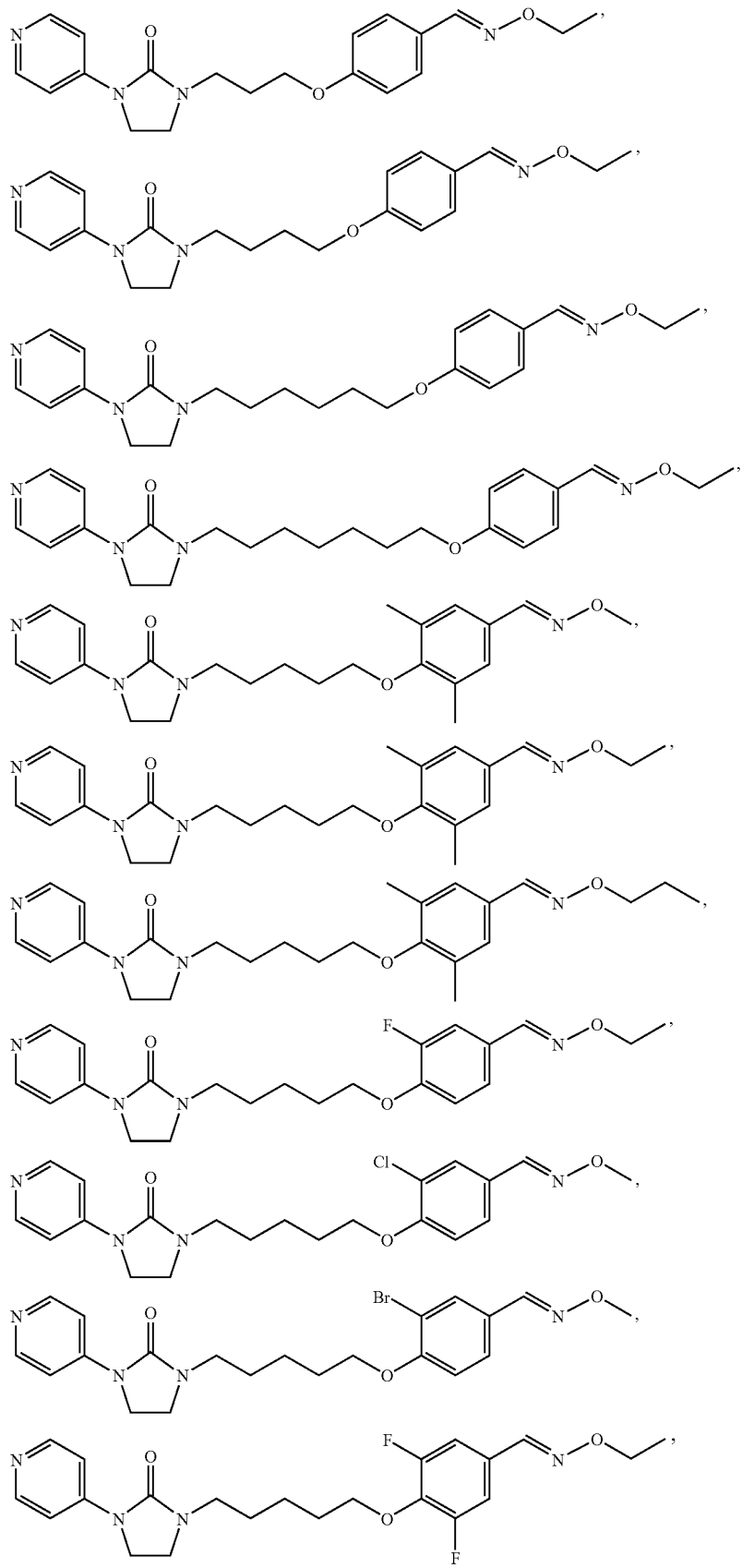

-continued
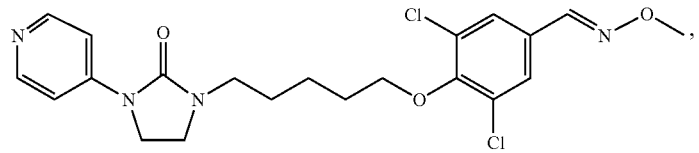,
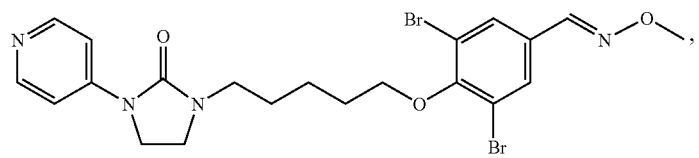,
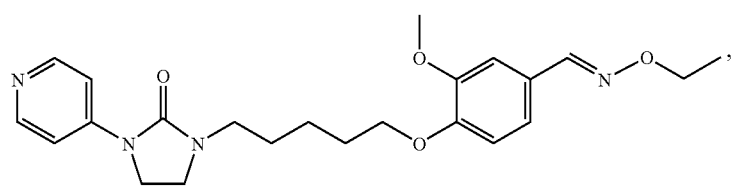,
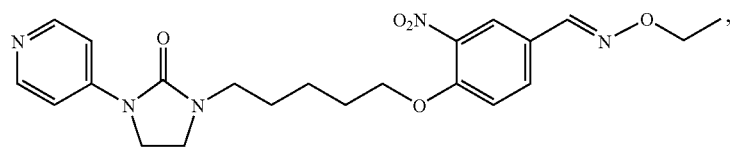,
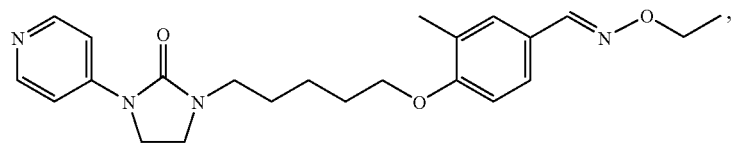,
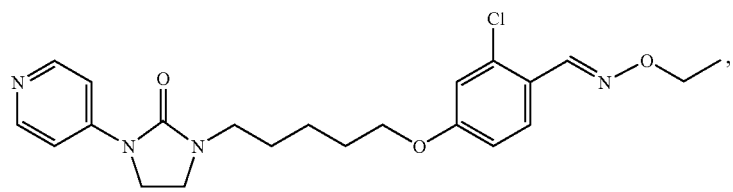,
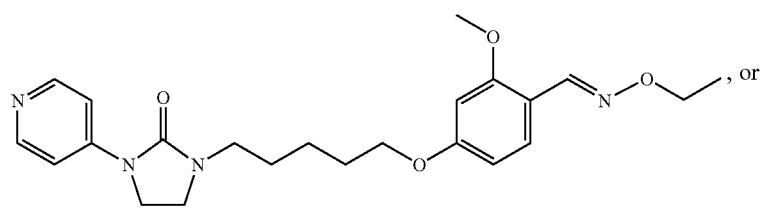, or
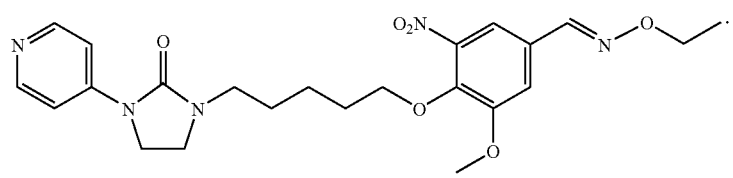;

13. A pharmaceutical composition of comprising a compound of the following formula:

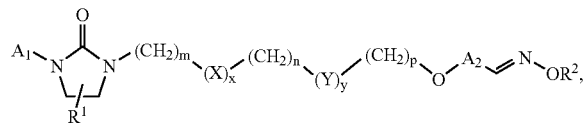

wherein

R$^1$ is H, halo, amino, cyano, nitro, alkyl, cycloalkyl, alkoxy, aryl, aralkyl, heterocycloalkyl, or heteroaryl;

R$^2$ is H, alkyl, cycloalkyl, aryl, aralkyl, heterocycloalkyl, or heteroaryl;

each of A$_1$ and A$_2$, independently, is aryl, aralkyl, or heteroaryl; provided that if A$_1$ is heteroaryl, A$_1$ is attached to the imidazolidinone ring via a C—N bond;

each of X and Y, independently, is —(CH$_2$)—, —C(H)(R$^a$), —C(R$^a$)(R$^b$)—, —NR$^c$—, —O—, —S—, —S(O)—, —S(O)$_2$—, aryl, cycloalkyl, heterocycloalkyl, heteroaryl, alkenyl, or alkynyl; each of R$^a$ and R$^b$, independently, being halo, alkyl, hydroxyalkyl, amino, alkoxy, mercapto, thioalkoxy, aryl, aralkyl, or heteroaryl; and R$^c$ being alkyl, aryl, aralkyl, cycloalkyl, heteroaryl, or heterocycloalkyl;

each of m, n, and p, independently, is 0, 1, 2, 3, 4, or 5; and each of x and y, independently, is 0 or 1; or a stereoisomer thereof.

14. The method of claim 13, wherein A$_1$ is 4-pyridyl.

15. The composition of claim 13, wherein A$_2$ is phenyl.

16. The composition of claim 13, wherein each of m and x is 0, y is 1, and Y is —(CH$^2$)—, —C(H)(R$^a$)—, or —C(R$^a$)(R$^b$)—, each of R$^a$ and R$^b$ being alkyl.

17. The composition of claim 13, wherein the compound is